(12) United States Patent
El-Zehiry

(10) Patent No.: US 10,424,411 B2
(45) Date of Patent: Sep. 24, 2019

(54) BIOPSY-FREE DETECTION AND STAGING OF CANCER USING A VIRTUAL STAGING SCORE

(71) Applicant: Siemens Healthcare GmbH, Erlangen (DE)

(72) Inventor: Noha Youssry El-Zehiry, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 748 days.

(21) Appl. No.: 15/309,165

(22) PCT Filed: Sep. 19, 2014

(86) PCT No.: PCT/US2014/056589
§ 371 (c)(1),
(2) Date: Nov. 4, 2016

(87) PCT Pub. No.: WO2015/042421
PCT Pub. Date: Mar. 26, 2015

(65) Prior Publication Data
US 2017/0116387 A1 Apr. 27, 2017

Related U.S. Application Data

(60) Provisional application No. 61/880,337, filed on Sep. 20, 2013.

(51) Int. Cl.
*G16H 50/30* (2018.01)
*G16H 50/70* (2018.01)
(Continued)

(52) U.S. Cl.
CPC .......... *G16H 50/30* (2018.01); *A61B 5/0066* (2013.01); *A61B 5/032* (2013.01); *A61B 5/037* (2013.01);
(Continued)

(58) Field of Classification Search
USPC .................................................. 382/128, 131
See application file for complete search history.

(56) References Cited

U.S. PATENT DOCUMENTS 8,812,240 B2 * 8/2014 Yu ........................ A61N 5/1031
702/19
9,536,054 B1 * 1/2017 Podilchuk ............. G06T 7/0012
(Continued)

FOREIGN PATENT DOCUMENTS

WO 2010115885 A1 10/2010
WO WO 2010/115885 * 10/2010 ............... G06T 7/00

OTHER PUBLICATIONS

Scheipers, Ulrich, et al. "Ultrasonic multifeature tissue characterization for prostate diagnostics." Ultrasound in medicine & biology 29.8 (2003): 1137-1149.
(Continued)

*Primary Examiner* — Ishrat I Sherali

(57) ABSTRACT

A method for predicting a cancer staging score from medical image data includes receiving patient data for a plurality of patients, where patient data for each of the plurality of patients includes one or more of an image volume of a suspected tumor in an organ, blood test data, demographic data, and ground truth tumor staging scores for the suspected tumor in the organ, extracting features from the patient data, and using the features extracted from the patient data to train a classifier to predict a cancer staging score for a new patient from one or more of an image volume of a suspected tumor in the organ, patient blood test data and patient demographic data of that new patient.

37 Claims, 6 Drawing Sheets

(51) Int. Cl.

| | |
|---|---|
| G16H 50/20 | (2018.01) |
| G06N 20/00 | (2019.01) |
| G06T 7/62 | (2017.01) |
| G06T 7/11 | (2017.01) |
| A61B 5/00 | (2006.01) |
| A61B 5/03 | (2006.01) |
| A61B 5/055 | (2006.01) |
| A61B 8/08 | (2006.01) |
| G06K 9/46 | (2006.01) |
| G06K 9/62 | (2006.01) |
| G06T 7/00 | (2017.01) |
| G06F 19/00 | (2018.01) |

(52) U.S. Cl.
CPC ............... *A61B 5/055* (2013.01); *A61B 8/08* (2013.01); *G06F 19/00* (2013.01); *G06K 9/4604* (2013.01); *G06K 9/6269* (2013.01); *G06N 20/00* (2019.01); *G06T 7/0012* (2013.01); *G06T 7/11* (2017.01); *G06T 7/62* (2017.01); *G16H 50/20* (2018.01); *G16H 50/70* (2018.01); *G06T 2207/10081* (2013.01); *G06T 2207/10088* (2013.01); *G06T 2207/10101* (2013.01); *G06T 2207/10104* (2013.01); *G06T 2207/10108* (2013.01); *G06T 2207/10132* (2013.01); *G06T 2207/30096* (2013.01); *G06T 2207/30101* (2013.01)

(56) References Cited

U.S. PATENT DOCUMENTS

| | | | | |
|---|---|---|---|---|
| 9,779,213 | B2* | 10/2017 | Donovan | G16H 50/50 |
| 9,870,614 | B1* | 1/2018 | Chou | A61B 5/055 |
| 10,185,890 | B2* | 1/2019 | Feiweier | A61B 5/0042 |
| 10,282,588 | B2* | 5/2019 | Comaniciu | G16H 30/00 |
| 2006/0018524 | A1* | 1/2006 | Suzuki | G06K 9/3233 382/128 |
| 2010/0121178 | A1* | 5/2010 | Krishnan | G06F 19/321 600/411 |
| 2010/0184093 | A1* | 7/2010 | Donovan | G16H 50/50 435/7.21 |
| 2013/0044927 | A1 | 2/2013 | Poole | |
| 2017/0032090 | A1* | 2/2017 | Kamen | G06N 7/005 |
| 2017/0091937 | A1* | 3/2017 | Barnes | C12Q 1/6886 |

OTHER PUBLICATIONS

Feleppa, Ernest J., et al. "Typing of prostate tissue by ultrasonic spectrum analysis." IEEE Transactions on Ultrasonics, Ferroelectrics, and Frequency Control 43.4 (1996): 609-619.

Wikipedia; Anonymous: "Gleason grading system", Wikipedia, Jul. 9, 2013 (Jul. 9, 2013), XP055521875; Retrieved from the Internet: URL:https://en.wikipedia.org/w/index.php?title=Gieason_grading_system&oldid=563496799[retrieved on Nov. 7, 2018].

Wikipedia, Anonymous: "Cancer staging", Wikipedia, Jun. 22, 2013 (Jun. 22, 2013), XP055521879, Retrieved from the Internet: URL:https://en.wikipedia.org/w/index.php?.

Wikipedia; Anonymous: "Grading (tumors)", Wikipedia, Mar. 6, 2013 (Mar. 6, 2013), XP055521870; Retrieved from the Internet: URL:https://en. wikipedia.org/w/index.php?title=Grading_(tumors)&oldid=.

Evangelia I. Zacharaki et al: "Classification of brain tumor type and grade using MRI texture and shape in a machine learning scheme", Magnetic Resonance in Medicine, vol. 62, No. 6, Oct. 26, 2009, pp. 1609-1618, XP055156156 / Oct. 26, 2009.

Cheng H D et al: "Automated breast cancer detection and classification using ultrasound images: A survey", Pattern Recognition, Elsevier, GB, vol. 43, No. 1, Jan. 1, 2010, pp. 299-317, XP026498170 / Jan. 1, 2010.

\* cited by examiner

| | |
|---|---|
| ANGULAR SECOND MOMENT | $\sum_i \sum_j p(i,j)^2$ |
| CONTRAST | $\sum_{n=0}^{N_a-1} n^2 \{ \sum_{i=1}^{N_a} \sum_{j=1}^{N_a} p(i,j) \}, |i-j| = n$ |
| CORRELATION | $\dfrac{\sum_i \sum_j (ij) p(i,j) - \mu_x \mu_y}{\sigma_x \sigma_y}$ |
| | WHERE $\mu_x$, $\mu_y$, $\sigma_x$, AND $\sigma_y$ ARE THE MEANS AND STD. DEVIATIONS OF $p_x$ AND $p_y$, THE PARTIAL PROBABILITY DENSITY FUNCTIONS |
| SUM OF SQUARES: VARIANCE | $\sum_i \sum_j (i - \mu)^2 p(i,j)$ |
| INVERSE DIFFERENCE MOMENT | $\sum_i \sum_j \dfrac{1}{1+(i-j)^2} p(i,j)$ |
| SUM AVERAGE | $\sum_{i=2}^{2N_a} x p_{x+y}(i)$ |
| | WHERE $x$ AND $y$ ARE THE COORDINATES (ROW AND COLUMN) OF AN ENTRY IN THE CO-OCCURRENCE MATRIX, AND $p_{x+y}(i)$ IS THE PROBABILITY OF CO-OCCURRENCE MATRIX COORDINATES SUMMING TO $x + y$ |
| SUM VARIANCE | $\sum_{i=2}^{2N_a} (i - f_8)^2 p_{x+y}(i)$ |
| SUM ENTROPY | $-\sum_{i=2}^{2N_a} p_{x+y}(i) \log\{p_{x+y}(i)\} = f_8$ |
| ENTROPY | $-\sum_i \sum_j p(i,j) \log(p(i,j))$ |
| DIFFERENCE VARIANCE | $-\sum_{i=0}^{N_a-1} x^2 p_{x-y}(i)$ |
| DIFFERENCE ENTROPY | $-\sum_{i=0}^{N_a-1} p_{x-y}(i) \log\{p_{x-y}(i)\}$ |
| INFO. MEASURE OF CORRELATION 1 | $\dfrac{HXY - HXY1}{\max\{HX, HY\}}$ |
| INFO. MEASURE OF CORRELATION 2 | $(1 - \exp[-2(HXY2 - HXY)])^{1/2}$ |
| | WHERE $HXY = -\sum_i \sum_j p(i,j) \log(p(i,j))$, $HX$, $HY$ ARE THE ENTROPIES OF $p_x$ AND $p_y$, $HXY1 = -\sum_i \sum_j p(i,j) \log\{p_x(i) p_y(j)\}$ $HXY2 = -\sum_i \sum_j p_x(i) p_y(j) \log\{p_x(i) p_y(j)\}$ |
| MAX. CORRELATION COEFF. | SQUARE ROOT OF THE SECOND LARGEST EIGENVALUE OF Q |
| | WHERE $Q(i,j) = \sum_k \dfrac{p(i,k) p(j,k)}{p_x(i) p_y(k)}$ |

FIG. 3

BIOPSY-FREE DETECTION AND STAGING OF CANCER USING A VIRTUAL STAGING SCORE

CROSS REFERENCE TO RELATED APPLICATIONS

This application is a 371 of international PCT/US2014/056589 filed Sep. 9, 2014 and claims benefit of U.S. provisional application No. 61/880,337 filed Sep. 20, 2013, the contents of which are herein incorporated by reference in their entirety.

TECHNICAL FIELD

This disclosure is directed to methods and systems for detecting cancer in medical images.

DISCUSSION OF THE RELATED ART

Prostate cancer is a challenging cancer to detect because its associated biopsy cannot consistently provide a uniform sampling of the prostate tissue and because of the very high false positive rate of the first diagnostic tests. The first diagnostic step in the detection of prostate cancer is a Prostate Specific Antigen (PSA) blood test. If the test shows an elevated PSA level, the physician typically recommends a biopsy. A prostate biopsy can be used to diagnose prostate cancer based on the Gleason score derived from the tissue appearance under a microscope. A tissue sample extracted from the prostate gland is examined by a pathologist who provides a Gleason score. The Gleason score is cancer staging score used to determine the aggressiveness of the disease. Cancers with higher Gleason score are more aggressive and have a worse prognosis.

There are some issues associated with this diagnostic pipeline. First, the PSA level test has a very high (80%) false positive rate. This may lead to unnecessary biopsies that can cause more harm than benefit. In fact, many patients may experience bleeding and/or hemorrhage due to unnecessary biopsies. Second, the prostate biopsy itself is not easy to perform. It is challenging to acquire samples from all the areas of the prostate, especially the peripheral zone where cancer most frequently occurs. In addition, a challenge associated with Gleason scoring is that the results depend on the location from which the tissue sample is acquired. In some cases, the biopsy/Gleason score results are inconclusive because the tissue is sampled from the wrong location. Similar issues occur concerning the detection of other types of cancer, such as breast cancer and lung cancer.

Prostate magnetic resonance (MR) imaging has shown promise in identifying regions that are highly likely to be cancerous. Researchers have investigated the correlation between pathological findings and imaging findings from MR data in particular, and the integration of information from other modalities such as ultrasound (US) and positron emission tomography (PET). MR has been used to guide biopsies, but it has not been effective at detecting the presence of cancer or determining its stage. Recently, integrated whole body PET/MRI systems have been introduced that can combine the anatomical information produced by MR images and the functional information provided by PET images, in a single setup, without the need for image registration. In prostate cancer in particular, novel research studies focusing on new tracers such as 11C-Choline and 11C-acetate have been proven to be more effective detecting and diagnosis the recurrence of prostate cancer than fluorodeoxyglucose (FDG), a tracer previously used in PET imaging. Therefore, combining PET with these new tracers with MR, which has been proven efficient in localizing prostate cancer candidates, is expected to change the way that prostate cancer is being diagnosed and treated.

SUMMARY

Exemplary embodiments of the disclosure as described herein are directed to biopsy-free methods for the early detection and staging of cancer using a virtual staging score. A method according to an embodiment of the disclosure uses an imaging based virtual staging score that can be completely calculated from image/patient information, non-invasively, without a biopsy, and that can replace the traditional staging score and plays the same role in the detection and diagnosis. Use of a virtual staging score according to an embodiment of the disclosure can eliminate the biopsy step that may cause bleeding, hemorrhaging and unnecessary complications in a patient. In addition, while prior art methods have focused on the recurrence of cancer, a virtual staging score according to an embodiment of the disclosure can be used for prediction the recurrence as well as the early detection. The use of a virtual staging score according to an embodiment of the disclosure can enable non invasive ways of detecting the cancer and may reduce the mortality rate from cancer. In the exemplary, non-limiting case of prostate cancer, a virtual Gleason score can be calculated using all the available information from one or more imaging modalities as well as patient demographic data and blood test results. Hence, it is expected to be more accurate than the PSA blood test and will eliminate the need for unnecessary biopsies and possibly unnecessary surgeries and complications.

According to an embodiment of the disclosure, there is provided a method for predicting a cancer staging score from medical image data, including receiving patient data for a plurality of patients, where patient data for each of the plurality of patients includes one or more of an image volume of a suspected tumor in an organ, blood test data, demographic data, and ground truth tumor staging scores for the suspected tumor in the organ, extracting features from the patient data, and using the features extracted from the patient data to train a classifier to predict a cancer staging score for a new patient from one or more of an image volume of a suspected tumor in the organ, patient blood test data and patient demographic data of that new patient.

According to a further embodiment of the disclosure, the image volume comprises one or more of an anatomical image volume, a functional image volume, or a fused anatomical/functional image volume, and features extracted from the image volume include one or more of anatomical features and functional features from the organ.

According to a further embodiment of the disclosure, extracting anatomical and functional features of the organ from the image volume includes segmenting the organ in each of the anatomical and functional images to define one or more regions of interest (ROIs), and extracting anatomical and functional features from the one or more regions of interest.

According to a further embodiment of the disclosure, a region of interest (ROI) is one of the whole organ or a segment of the organ.

According to a further embodiment of the disclosure, anatomical features include a volume of an ROI, a surface area of the ROI, a diameter of the ROI, texture features associated with the ROI, and geometric descriptors of the surface of the ROI.

According to a further embodiment of the disclosure, texture features are calculated from a Gray Level Co-occurrence Matrix of the ROI.

According to a further embodiment of the disclosure, functional features include a standard uptake value, an apparent diffusion coefficient, a permeability surface area product per unit volume of tissue, a fraction of plasma per unit volume of tissue, and a rate constant of an efflux of contrast media from extracellular space back to plasma.

According to a further embodiment of the disclosure, features from the patient demographic data include a patient's weight, height, age, body mass index, body surface area, organ size, any past history of cancer occurrence, and any health index test results.

According to a further embodiment of the disclosure, imaging modalities that capture anatomical information include magnetic resonance imaging (MRI), computed tomography (CT), ultrasound (US), optical coherence tomography (OCT), imaging modalities that capture functional information include positron emission tomography (PET), single photon emission computed tomography (SPECT), dynamic contrast enhanced MRI (DCE-MRI), and diffusion weighted MRI (DW-MRI), and a fused anatomical/functional modality that captures anatomical and functional information includes any combination of a modality that captures anatomical information and a modality that captures functional information.

According to a further embodiment of the disclosure, the classifier is trained using an image-based boosting ridge regression method.

According to a further embodiment of the disclosure, the classifier predicts a local staging score for each segment or ROI of the organ and a global staging score by combining local staging scores for each segment or ROI.

According to a further embodiment of the disclosure, the organ is a prostate gland, image features are extracted from a fused MR/PET image, features from the blood test data include a prostate specific antigen (PSA) level, a PSA velocity, a PSA density, and a prostate health index, and the predicted cancer staging score is a Gleason score.

According to a further embodiment of the disclosure, the organ is a lung, image features are extracted from a fused MR/PET image, and the predicted cancer staging score is a TNM score.

According to a further embodiment of the disclosure, the organ is a breast, image features are extracted from a fused MR/PET image, and the predicted cancer staging score is one of a Nottingham Score or a Scarf-Bloom-Richardson Score.

According to another embodiment of the invention, there is provided a method of predicting a cancer staging score from medical image data, including receiving patient data for a patient, where the patient data for the patient includes one or more of an image volume of a suspected tumor in an organ, blood test data, and demographic data, extracting features from the patient data, and providing the features to a classifier, where the classifier predicts a cancer staging score that is indicative of whether the patient's organ is cancerous.

According to a further embodiment of the disclosure, the image volume comprises one of an anatomical image volume, a functional image volume, or a fused anatomical/functional image volume, and features extracted from the image volume include one or more of anatomical and functional features from the organ.

According to a further embodiment of the disclosure, imaging modalities that capture anatomical information include magnetic resonance imaging (MRI), computed tomography (CT), ultrasound (US), optical coherence tomography (OCT), imaging modalities that capture functional information include positron emission tomography (PET), single photon emission computed tomography (SPECT), dynamic contrast enhanced MRI (DCE-MRI), and diffusion weighted MRI (DW-MRI), and a fused anatomical/functional modality that captures anatomical and functional information includes any combination of a modality that captures anatomical information and a modality that captures functional information.

According to a further embodiment of the disclosure, extracting anatomical and functional features from the image volume includes segmenting the organ in the anatomical and functional images to define one or more regions of interest (ROIs), and extracting anatomical and functional features from the one or more regions of interest, where a region of interest is one of the whole organ or a subregion of the organ.

According to a further embodiment of the disclosure, the classifier predicts a local staging score for each ROI of the organ and a global staging score by combining local staging scores for each ROI.

According to a further embodiment of the disclosure, the classifier is trained using one or more of features extracted from a plurality of image volumes of the organ, features extracted from a plurality of patient blood test results, features extracted from patient demographic data, and a plurality of ground truth staging scores from a plurality of organ biopsies.

According to a further embodiment of the disclosure, the classifier is trained using an image-based boosting ridge regression method.

According to a further embodiment of the disclosure, each of the plurality of image volume comprises one or more of an anatomical image volume, a functional image volume, or a fused anatomical/functional image volume, and features extracted from the image volume include one or more of anatomical features and functional features from the organ.

According to a further embodiment of the disclosure, the organ is a prostate gland, image features are extracted from a fused MR/PET image, features from the blood test data include a prostate specific antigen (PSA) level, a PSA velocity, a PSA density, and a prostate health index, and the predicted cancer staging score is a Gleason score.

According to a further embodiment of the disclosure, the organ is a lung, image features are extracted from a fused MR/PET image, and the predicted cancer staging score is a TNM score.

According to a further embodiment of the disclosure, the organ is a breast, image features are extracted from a fused MR/PET image, and the predicted cancer staging score is one of a Nottingham Score or a Scarf-Bloom-Richardson Score.

According to a another embodiment of the disclosure, there is provided a non-transitory program storage device readable by a computer, tangibly embodying a program of instructions executed by the computer to perform the method steps for predicting a cancer staging score from medical image data.

BRIEF DESCRIPTION OF THE DRAWINGS

FIG. 3 is a table of texture features associated with an ROI that can be calculated from a GLCM, according to an embodiment of the disclosure.

DETAILED DESCRIPTION OF EXEMPLARY EMBODIMENTS

Figure 1:
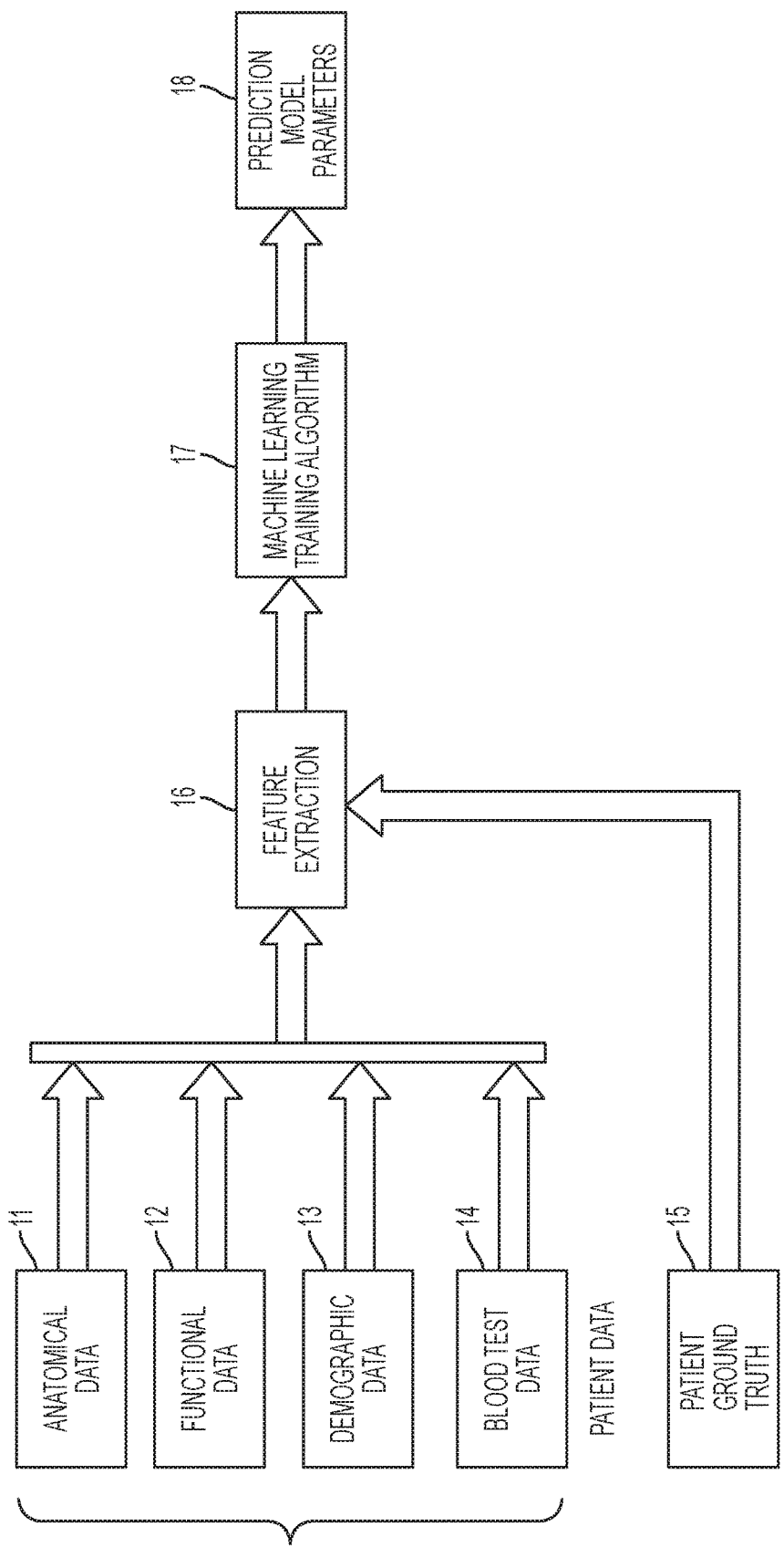
FIG. 1 is a schematic block diagram of a training phase according to an embodiment of the disclosure.

Exemplary embodiments of the disclosure as described herein generally include systems and methods for a biopsy-free early detection and staging of prostate cancer using a virtual Gleason score. Accordingly, while the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to $R$ or $R^7$, the methods of the disclosures are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Prostate cancer is interesting because of the challenges associated with a biopsy that cannot consistently provide a uniform sampling of the prostate tissue and because of the very high false positive rate of the PSA test. Embodiments of the disclosure are directed to biopsy-free methods for the detection and staging of cancer using a virtual staging score, and are described herein below using prostate cancer and its associated Gleason score as exemplary, non-limiting examples. However, embodiments of the disclosure can be applied to other oncology applications, as breast or lung cancer, to evaluate a cancer staging score, such as the Nottingham histological score or TNM staging score. For example, embodiments of the disclosure can be applied to breast cancer and can use the scoring system that is currently used to stage breast cancer based on biology. Methods according to embodiments of the disclosure can be used to predict the Scarf-Bloom-Richardson Score or the Nottingham histologic score, which is a modification of the Scarf-Bloom-Richardson Score, or any other scoring system that deduces the cancer stage from pathology. For example, the TNM score for lung cancer can be predicted by a system according to an embodiment of the disclosure A method according to an embodiment of the disclosure for a non invasive imaging based technique for the early detection of prostate cancer as well as the staging and the post surgery follow up may be based on an investigation of the correlation between the Gleason index and the patient feature vector computed from the integration of anatomical imaging, functional imaging, patient demographics and or patient previous tests. Prostate Scans are used to analyze the appearance, texture, and morphology of the prostate in the acquired images to determine the relationship between these features and the Gleason score. The patient features and the Gleason index can be used to train a classifier using a combined feature vector to calculate a "Virtual Gleason Score" and use it early detect prostate cancer or to predict the aggressiveness of the disease. In an exemplary, non-limiting embodiment, a fused MR/PET can be used to calculate the image associated feature vector. In general, the feature vector uses features calculated from image data, such as MR, CT, PET, MR/PET, DW-MR, DCE-MR, US data, or any another modality that can provide anatomical or functional information of the prostate.

Methods according to embodiments of the disclosure include two phases: a training phase and a prediction phase. FIG. 1 is a schematic block diagram of a training phase according to an embodiment of the disclosure. A training phase according to an embodiment of the disclosure uses features 16 extracted from patient data that includes one or more of imaging information, such as MR/PET anatomical 11 and functional 12 data for a patient, patient information, such as demographic 13 and blood test 14 data, well as the ground truth information 15 for a Gleason score calculated from biopsies, to train a classifier 17. Thus, classifier may be trained with any combination or subset of the imaging (anatomical and/or functional) data, blood test data, and demographic data, or with all of that data. According to other embodiments of the disclosure, other modalities, such as single-photon emission computed tomography (SPECT), computed tomography (CT), CT/PET, etc., may also be used to derive image based information. A training phase according to an embodiment of the disclosure outputs parameters 18 of the predication model, referred to as the classifier parameters, that can be subsequently used to compute the Gleason score for a new patient who has not had a biopsy.

Figure 2:
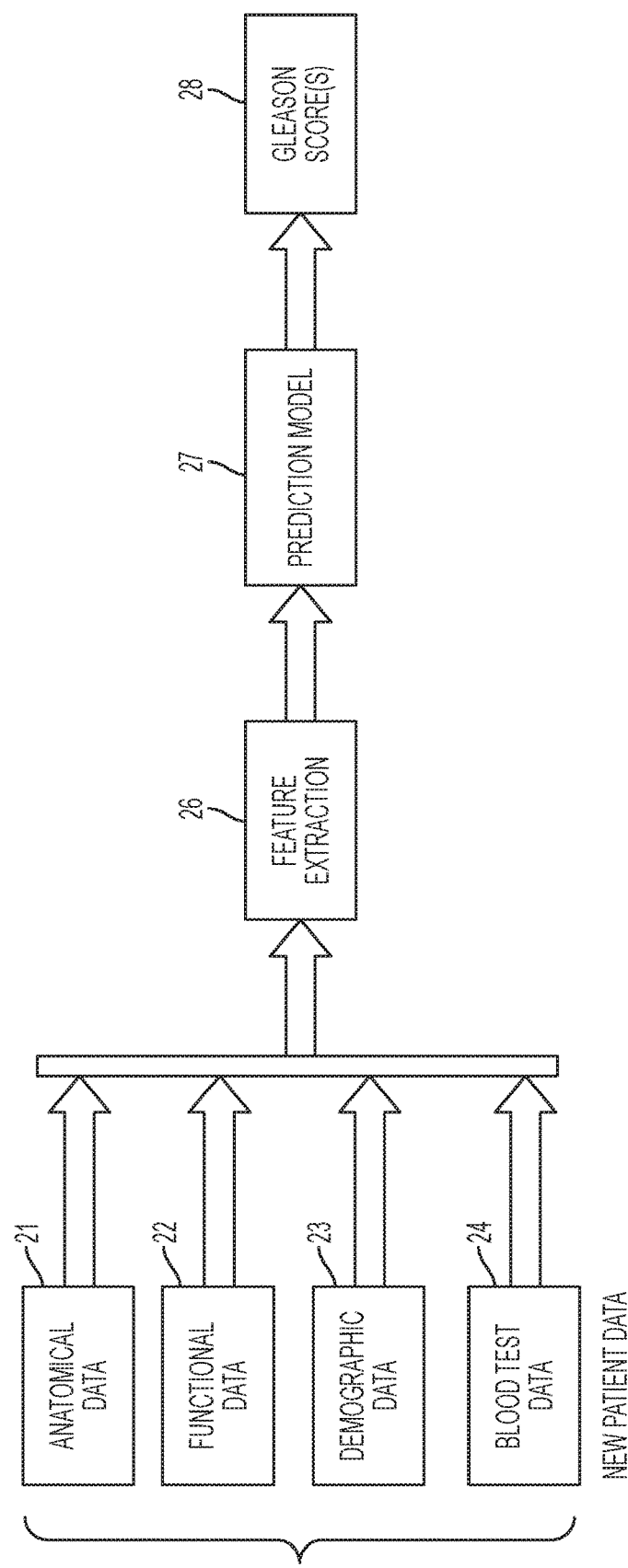
FIG. 2 is a schematic block diagram of a prediction/execution phase according to an embodiment of the disclosure.

FIG. 2 is a schematic block diagram of a prediction/execution phase according to an embodiment of the disclosure. In a prediction/execution phase according to an embodiment of the disclosure, given a new patient who has not had a biopsy, features 26, such as anatomical 21 and functional 22 data, are extracted from imaging data of the patient, and from patient information, such as demographic 23 and blood test 24 data, and these features 26 are used as input to the predication model 27 obtained from a training phase according to an embodiment of the disclosure. Similar to the training phase, a classifier according to an embodiment of the invention can predict a virtual Gleason score from any combination or subset of the anatomical data, the functional data, the demographic data, and the blood test data, or from all of that data. Accordingly, a prediction model according to an embodiment of the disclosure can output a Virtual Gleason score 28.

List of Proposed Features

According to an embodiment of the disclosure, a mixture of features may be used to characterize each patient and capture all the available information. This mixture may include anatomical information, functional information, blood diagnostic data and patient demographics.

Anatomical features can be derived from one or more imaging modalities, such as computed tomography (CT), magnetic resonance imaging (MRI), ultrasound (US), optical coherence tomography (OCT), etc.

Functional features can also be derived from one or more imaging modalities that reflect functional information, such as: positron emission tomography (PET), single photon emission computed tomography (SPECT), dynamic contract enhanced magnetic resonance imaging (DCE-MRI), diffusion weighted magnetic resonance imaging (DW-MRI), etc.

According to an embodiment of the disclosure, this information can be integrated from any combination of modalities. Some imaging scanners can provide simultaneous acquisition of anatomical/functional images with combined modalities such as PET/CT and more recently PET/MR.

In an exemplary, non-limiting embodiment, the features are extracted from MR/PET, however, any other modality or combination of modalities can be used for extracting the image based features. Based on the imaging modality/modalities used, the extracted features may be binary, numerical, categorical, etc.

A list of features that can be computed from the anatomical images includes:
  Volume of a region of interest (ROI)
  Surface Area of ROI
  Diameter of ROI.
  Texture features associated with ROI
  Geometric descriptor of the surface of ROI
    Mean curvature
    Gaussian curvature
    Curvedness $\sqrt{(\kappa_1^2+\kappa_2^2)/2}$, where $\kappa_1$ and $\kappa_2$ are the principle curvatures
    Shape index:

$$\frac{2}{\pi}\tan^{-1}\left(\frac{\kappa_1 + \kappa_2}{\kappa_1 - \kappa_2}\right)$$

Texture features may be calculated from the Gray Level Co-occurrence Matrix (GLCM), which is a matrix that represents the co-occurrence of all possible pairs of gray levels. This matrix is square with dimension $N_g$, where $N_g$ is the number of gray levels in the image. Element [i, j] of the matrix is generated by counting the number of times a pixel with value i is adjacent to a pixel with value j and then dividing the entire matrix by the total number of such comparisons. Thus, each entry p(i, j) may be considered to be the probability that a pixel with value i will be found adjacent to a pixel with value j. The GLCM may be represented as $$G = \begin{bmatrix} p(1,1) & p(1,2) & \ldots & p(1,N_g) \\ p(2,1) & p(2,2) & \ldots & p(1,N_g) \\ \vdots & \vdots & \ddots & \vdots \\ p(N_g,1) & p(N_g,2) & \ldots & p(N_g,N_g) \end{bmatrix}$$

The GLCM can be calculated in several directions. Since adjacency can occur in each of 26 directions in a 3D rectangular image volume, 26 such matrices can be calculated.

There are 14 known texture features that may be calculated from the GLCM. These are listed in FIG. 3. Texture features may also be represented as local binary patterns.

Features that can be computed from the functional images include:
  Standard Uptake Value (SUV) (PET images).
  ADC (Apparent Diffusion Coefficient) (Diffusion Weighted MR images).
  $K_{trans}$: the permeability surface area product per unit volume of tissue, which determines the flux from the intravascular space to the extracellular space (Dynamic Contrast Enhanced (DCE)-MR)
  $V_e$: the fraction of plasma per unit volume of tissue (DCE-MR)
  $K_{ep}$: the rate constant describing the efflux of contrast media from extracellular space back to plasma (DCE-MR)

A list of features that can be extracted from patient blood tests includes:
  PSA (Prostate Specific Antigen) level
  PSA velocity.
  PSA density.
  PHI (Prostate Health Index)

A list of features that can be extracted from the patient demographics include:
  Weight
  Height
  Age
  Body Mass Index (BMI)
  Body Surface Area (BSA)
  Prostate size
  Past history of prostate cancer occurrence (if any)
  Past measurements of PSA and PHI test results (if any)

A machine learning algorithm according to an embodiment of the disclosure may use all the previous features or a subset of the previous features for training and prediction/execution. In addition, according to embodiments of the disclosure, any linear or nonlinear combination of the subsets of features may also be used for training and prediction.

Moreover, methods according to embodiments of the disclosure may train different classifiers based on different subsets or combinations of features to accommodate any missing features in the prediction phase.

In a prediction phase according to an embodiment of the disclosure, one or more classifiers can be used to determine the virtual Gleason score. Moreover, rules may be enforced for choosing a classifier for the prediction phase, or a weighted linear or non-linear combination of the results of multiple classifiers may be used to determine the final predicted virtual Gleason score.

Feature Extraction—ROI Definition

A region-of-interest (ROI) according to an embodiment of the disclosure can be the whole prostate, a subset of the prostate where a suspected tumor exists, or a partition of the prostate into disjoint sets where each set represent an ROI.

According to an embodiment of the disclosure, initially the prostate is segmented. The segmentation of the prostate may be performed manually, in which a user interacts with a visualization platform to highlight the prostate boundaries/inner voxels. Segmentation can also be performed semi automatically, where a user highlights some voxels of the prostate and a segmentation algorithm outputs a full prostate segmentation. Segmentation can also be performed automatically.

After segmenting the prostate, an ROI (s) can be defined in at least three different ways.

Manually: The user interacts with a visualization system and manually draws the region of interest.

Automatic/Semi automatic: The user highlights part of the ROI and an imaging based optimization algorithm computes the ROI boundaries based on the image features. Algorithms such as graph cuts, random walker, Mumford-Shah, and level sets can be used to perform this optimization task.

Anatomical Partitioning: The prostate can be subdivided into disjoint segments that represent different anatomical zones in the prostate. Each segment may be considered an ROI. The prostate can be subdivided into 16 or 27 disjoint segments, as shown in FIGS. 4(A)-(B).

Figure 4:
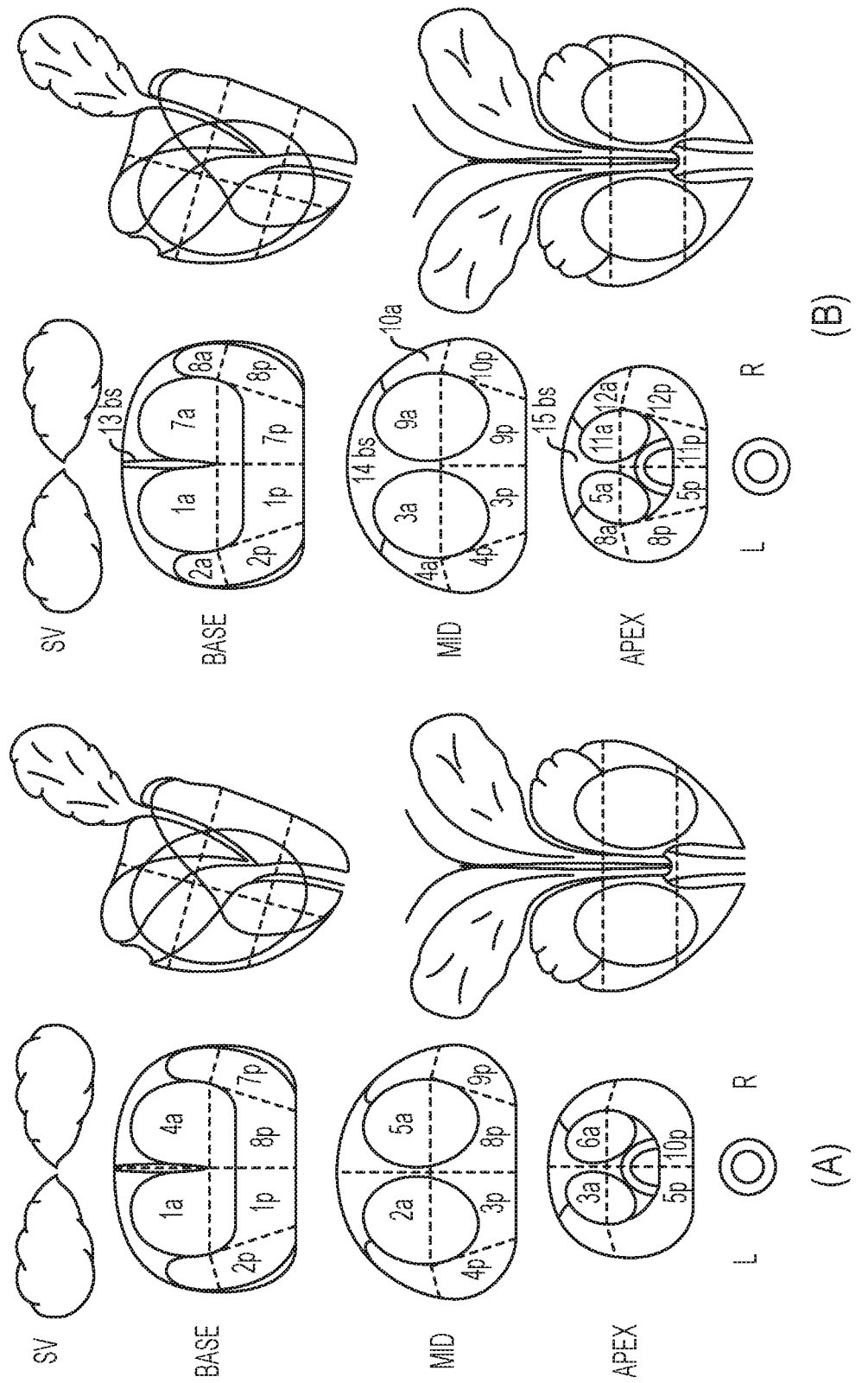
FIGS. 4(A)-(B) illustrate different subdivisions of the prostate into 16 or 27 disjoint segments, according to an embodiment of the disclosure.

FIG. 4(A) shows 16 regions/sectors of a standardized MRI prostate reporting scheme. Posteriorly (p), average axial sections at the prostate base and midgland are subdivided into 4 regions (midlobar and lateral) and at the prostate apex into 2 regions. Anteriorly (a), the prostate base, midgland, and apex are divided into 2 regions. There are thus 10 posterior glandular regions and 6 anterior glandular and stromal regions. The anterior region starts 17 mm from the prostatic posterior surface. A 10-core extended biopsy scheme would be expected to sample the 10 posterior sectors. FIG. 4(B) shows 27 regions/sectors of another standardized MRI prostate reporting scheme. Posteriorly (p), average axial sections at the prostate base, midgland and apex are subdivided into 4 regions (midlobar and lateral). Anteriorly (a), the prostate is divided into 4 anterior regions (midlobar and lateral) and 3 anterior stroma regions (as). There are thus 12 posterior and 12 anterior glandular regions, and 3 anterior stroma central regions. The anterior region starts 17 mm from the prostatic posterior surface. A 12-core extended biopsy scheme would be expected to sample the 12 posterior sectors. The reference label "SV" in the images refers to the seminal vesicle.

Feature Extraction from ROI

According to embodiments of the disclosure, feature extraction can be performed in at least three ways: fully automatic feature extraction, semi-automatic feature extraction, or manual feature extraction.

A combination of methods may be used, i.e. some futures can be extracted manually by a user while others may be extracted semi-automatically based on the interaction.

Automatic feature extraction: in an automatic scenario according to an embodiment of the disclosure, an algorithm can extract all features. For example, the maximum diameter of an ROI can be computed automatically.

Manual feature extraction: in an opposing scenario, a user may interact with a visualization platform to draw the maximum diameter in one or more directions of a 3D ROI.

Semi-automatic feature extraction: a combination of the automatic and manual can yield a semi-automatic feature extraction that utilizes a user's interaction to compute some of the features.

Constructing a Predictive Model Using Machine Learning

Once features are extracted and a ground truth is assembled, there is all the necessary information to construct a predictive model according to an embodiment of the disclosure For each patient, there is a feature vector that includes the set of extracted features and the ground truth Gleason score from the biopsy. Information for all patients is input to a machine learning algorithm to learn a mapping between the feature vectors and the Gleason scoring. The learning approach can be fully supervised, semi-supervised, transductive or reinforcement learning.

Transductive learning is reasoning from observed, specific (training) cases to specific (test) cases. This differs from supervised learning in that all or specific training cases are used to learn general rules. Reinforcement learning (RL) is learning by interacting with an environment. An RL agent learns from the consequences of its actions, rather than from being explicitly taught and it selects its actions on basis of its past experiences and also by new choices, which is essentially trial and error learning. The reinforcement signal that an RL-agent receives is a numerical reward, which encodes the success of an action's outcome, and the agent learns to select actions that maximize the accumulated reward over time.

According to an embodiment of the disclosure, an image-based boosting ridge regression method may be used to train a classifier.

According to an embodiment of the disclosure, the complexity of the output manifold that relates the functional parameters to the input measurements can be captured by extending an image-based boosting ridge regression (IBRR) method described in U.S. Pat. No. 7,949,173, the contents of which are herein incorporated by reference in their entirety. The method can encapsulate the non-linear relationships between image features, image context information and anatomical object parameters.

Alternatively, according to other embodiments of the disclosure, other machine learning algorithms may also be used, ranging from regression (linear, non-linear, logistic), decision-trees or graphs, association rule learning, artificial neural networks, support-vector machines, inductive logic programming, Bayesian networks, instance-based learning, manifold learning, sub-space learning, deep learning, dictionary learning, etc.

Embodiments of the disclosure can provide a localized Gleason score for each prostate segment, varying from 16 segments to 27 segments, in the different prostate zones. Further embodiments of the disclosure can provide a global Gleason Score by combining the local Gleason scores in the different segments. In addition, further embodiments of the disclosure can provide a localization of a region of interest based on the localized scores and the image features.

Workflows

According to embodiments of the disclosure, there are several possible workflows for a prediction phase of an embodiment of the disclosure. An exemplary, non-limiting embodiment uses anatomical and functional imaging information based on a combined MR/PET imaging modality. Within this embodiment, at least three possible workflows may be considered, which vary in the amount of computation performed on the scanner versus the computational workstation.

In a first workflow, all processing steps, such as image acquisition, feature extraction and virtual Gleason score computation are performed on the scanner. In a second workflow, the image acquisition is performed on the scanner, the images are transferred to the workstation, and feature extraction and score prediction are performed on the workstation. In a third workflow, image acquisition as well as feature extraction are performed on the scanner, while the output feature vector is transferred to the workstation where the virtual Gleason score prediction is computed.

Figure 5:
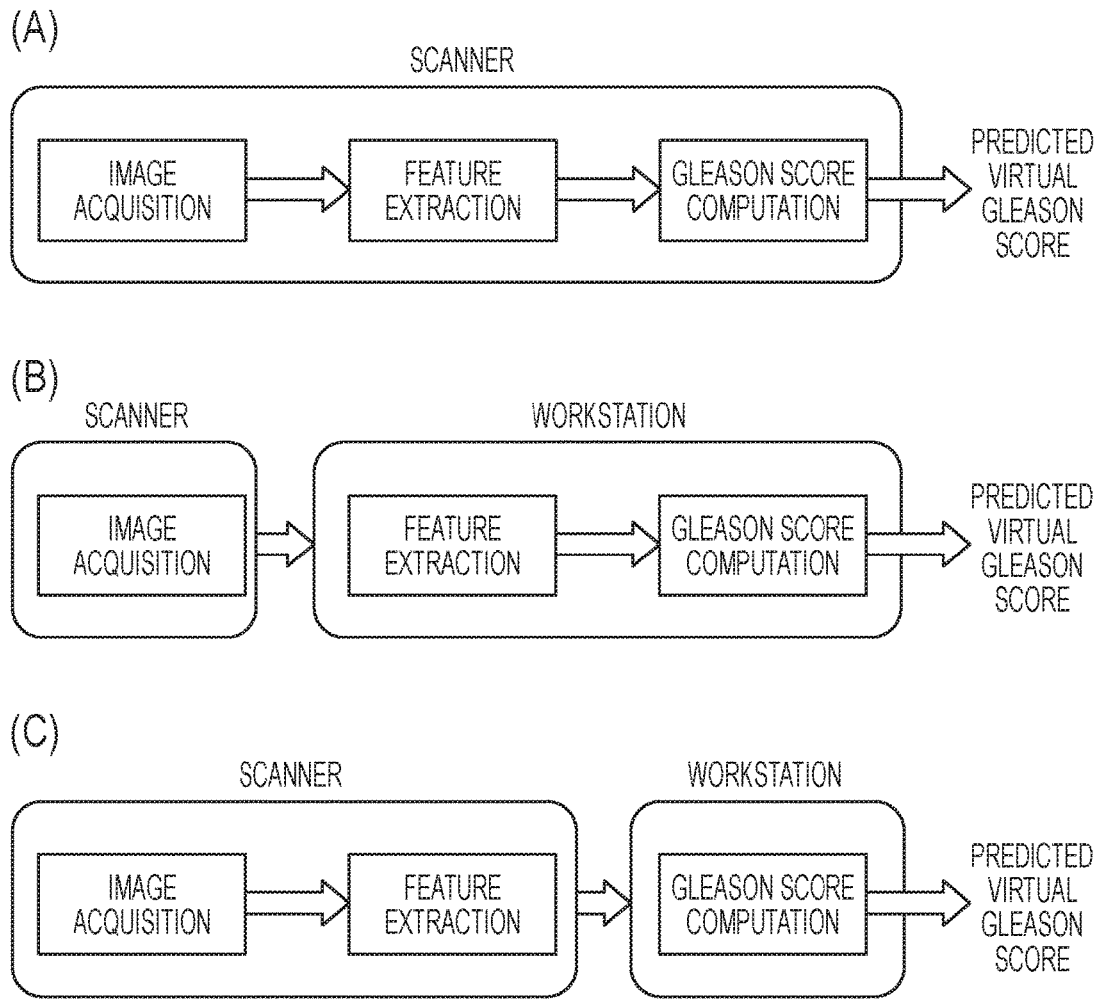
FIGS. 5(A)-(C) is a block diagram of three possible workflows, according to an embodiment of the disclosure.

FIGS. 5(A)-(C) is a block diagram of three possible workflows. FIG. 5(A) shows all processing being performed on the scanner; FIG. 5(B) shows the image being transferred to the workstation, and feature extraction and score prediction being performed on the scanner; and FIG. 5(C) shows feature extraction being performed on the scanner, the feature vector being transferred to the workstation and prediction being performed on the workstation.

System Implementations

It is to be understood that embodiments of the present disclosure can be implemented in various forms of hardware, software, firmware, special purpose processes, or a combination thereof. In one embodiment, the present disclosure can be implemented in software as an application program tangible embodied on a computer readable program storage device. The application program can be uploaded to, and executed by, a machine comprising any suitable architecture.

Figure 6:
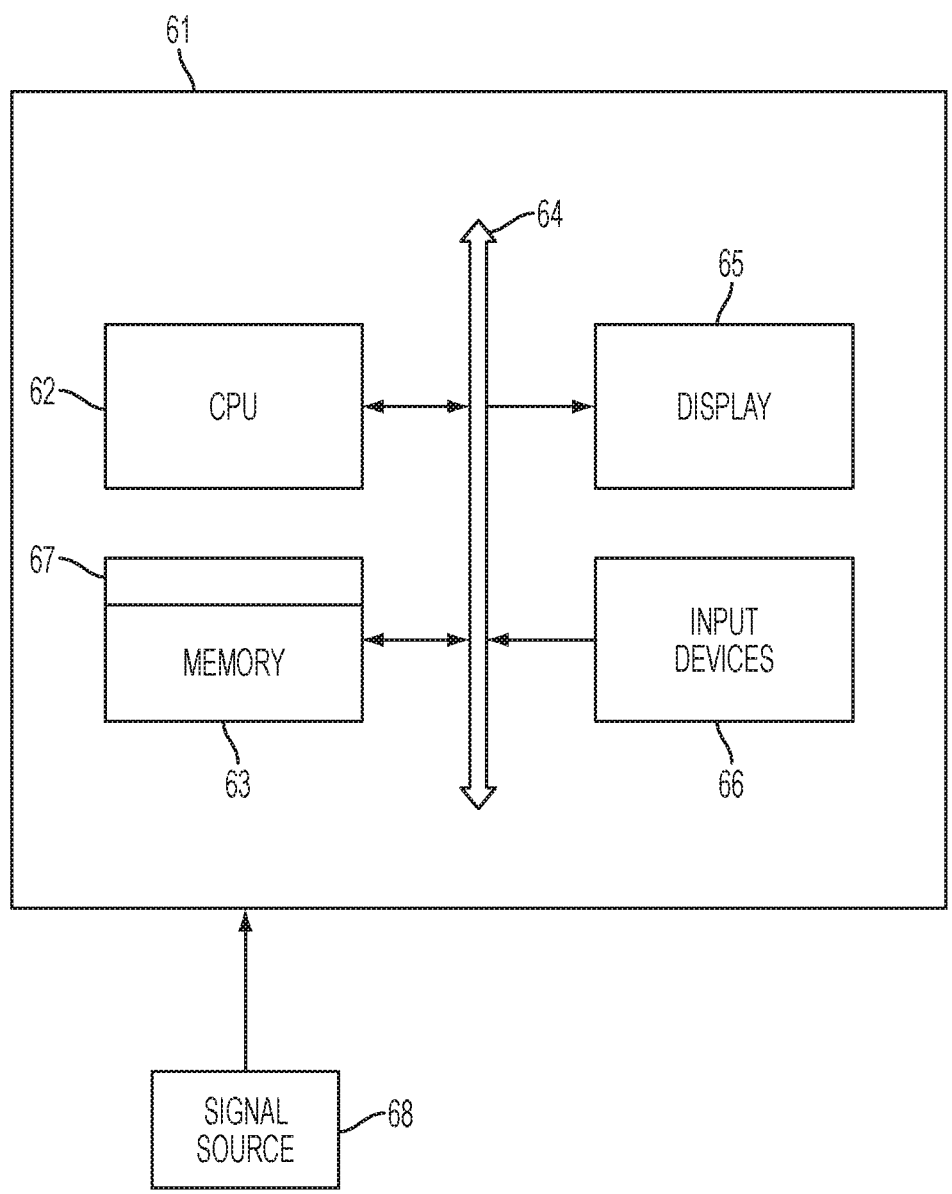
FIG. 6 is a block diagram of an exemplary computer system for implementing a biopsy-free method for the early detection and staging of cancer using a virtual staging score, according to an embodiment of the disclosure.

FIG. 6 is a block diagram of an exemplary computer system for implementing a biopsy-free method for the early detection and staging of prostate cancer using a virtual Gleason score, according to an embodiment of the disclosure. Referring now to FIG. 6, a computer system 61 for implementing the present disclosure can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present disclosure can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present disclosure.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present disclosure is programmed. Given the teachings of the present disclosure provided herein, one of ordinary skill in the related art will be able to contemplate these and similar implementations or configurations of the present disclosure.

While the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A computer-implemented method of predicting a cancer staging score from medical image data, the method comprising the steps of:
receiving patient data for a plurality of patients, wherein patient data for each of said plurality of patients includes one or more of an image volume of a suspected tumor in an organ, blood test data, demographic data, and ground truth tumor staging scores for the suspected tumor in said organ;
extracting features from said patient data, wherein features from said demographic data include a patient's weight, height, age, body mass index, body surface area, organ size, any past history of cancer occurrence, and any health index test results; and
using the features extracted from said patient data to train a classifier to predict a cancer staging score for a new patient from one or more of an image volume of a suspected tumor in said organ, patient blood test data and patient demographic data of that new patient.

2. The method of claim 1, wherein the image volume comprises one or more of an anatomical image volume, a functional image volume, or a fused anatomical/functional image volume, and features extracted from said image volume include one or more of anatomical features and functional features from said organ.

3. The method of claim 2, wherein extracting anatomical and functional features of said organ from said image volume comprises:
segmenting the organ in each of the anatomical and functional images to define one or more regions of interest (ROIs); and
extracting anatomical and functional features from the one or more regions of interest.

4. The method of claim 3, wherein a region of interest (ROI) is one of the whole organ or a segment of the organ.

5. The method of claim 2, wherein anatomical features include a volume of an ROI, a surface area of the ROI, a diameter of the ROI, texture features associated with the ROI, and geometric descriptors of a surface of the ROI.

6. The method of claim 5, wherein texture features are calculated from a Gray Level Co-occurrence Matrix of the ROI.

7. The method of claim 2, wherein functional features include a standard uptake value, an apparent diffusion coefficient, a permeability surface area product per unit volume of tissue, a fraction of plasma per unit volume of tissue, and a rate constant of an efflux of contrast media from extracellular space back to plasma.

8. The method of claim 2, wherein imaging modalities that capture anatomical information include magnetic resonance imaging (MRI), computed tomography (CT), ultrasound (US), optical coherence tomography (OCT), imaging modalities that capture functional information include positron emission tomography (PET), single photon emission computed tomography (SPECT), dynamic contrast enhanced MRI (DCE-MRI), and diffusion weighted MR1 (DW-MR1), and a fused anatomical/functional modality that captures anatomical and functional information includes any combination of a modality that captures anatomical information and a modality that captures functional information.

9. The method of claim 1, wherein the classifier is trained using an image-based boosting ridge regression method.

10. The method of claim 3, wherein said classifier predicts a local staging score for each segment or ROI of the organ and a global staging score by combining local staging scores for each segment or ROI.

11. The method of claim 1, wherein the organ is a prostate gland, image features are extracted from a fused MR/PET image, features from said blood test data include a prostate specific antigen (PSA) level, a PSA velocity, a PSA density, and a prostate health index, and the predicted cancer staging score is a Gleason score.

12. The method of claim 1, wherein the organ is a lung, image features are extracted from a fused MR/PET image, and the predicted cancer staging score is a TNM score.

13. The method of claim 1, wherein the organ is a breast, image features are extracted from a fused MR/PET image, and the predicted cancer staging score is one of a Nottingham Score or a Scarf-Bloom-Richardson Score.

14. A computer-implemented method of predicting a cancer staging score from medical image data, the method implemented by the computer comprising the steps of:
receiving patient data for a patient, wherein said patient data for the patient includes one or more of an image volume of a suspected tumor in an organ, blood test data, and demographic data;
extracting features from said patient data, wherein features from said demographic data include a patient's weight, height, age, body mass index, body surface area, organ size, any past history of cancer occurrence, and any health index test results; and
providing said features to a classifier, wherein said classifier predicts a cancer staging score that is indicative of whether the patient's organ is cancerous.

15. The method of claim 14, wherein the image volume comprises one of an anatomical image volume, a functional image volume, or a fused anatomical/functional image volume, and features extracted from said image volume include one or more of anatomical and functional features from said organ.

16. The method of claim 15, wherein imaging modalities that capture anatomical information include magnetic resonance imaging (MRI), computed tomography (CT), ultrasound (US), optical coherence tomography (OCT), imaging modalities that capture functional information include positron emission tomography (PET), single photon emission computed tomography (SPECT), dynamic contrast enhanced MRI (DCE-MRI), and diffusion weighted MRI (DW-MRI), and a fused anatomical/functional modality that captures anatomical and functional information includes any combination of a modality that captures anatomical information and a modality that captures functional information.

17. The method of claim 15, wherein extracting anatomical and functional features from said image volume comprises:
segmenting the organ in said anatomical and functional images to define one or more regions of interest (ROIs); and
extracting anatomical and functional features from the one or more regions of interest,
wherein a region of interest is one of the whole organ or a subregion of the organ.

18. The method of claim 17, wherein said classifier predicts a local staging score for each ROI of the organ and a global staging score by combining local staging scores for each ROI.

19. The method of claim 14, wherein the classifier is trained using one or more of features extracted from a plurality of image volumes of said organ, features extracted from a plurality of patient blood test results, features extracted from patient demographic data, and a plurality of ground truth staging scores from a plurality of organ biopsies.

20. The method of claim 19, wherein the classifier is trained using an image-based boosting ridge regression method.

21. The method of claim 19, wherein each of the plurality of image volume comprises one or more of an anatomical image volume, a functional image volume, or a fused anatomical/functional image volume, and features extracted from said image volume include one or more of anatomical features and functional features from said organ.

22. The method of claim 14, wherein the organ is a prostate gland, image features are extracted from a fused MR/PET image, features from said blood test data include a prostate specific antigen (PSA) level, a PSA velocity, a PSA density, and a prostate health index, and the predicted cancer staging score is a Gleason score.

23. The method of claim 14, wherein the organ is a lung, image features are extracted from a fused MR/PET image, and the predicted cancer staging score is a TNM score.

24. The method of claim 14, wherein the organ is a breast, image features are extracted from a fused MR/PET image, and the predicted cancer staging score is one of a Nottingham Score or a Scarf-Bloom-Richardson Score.

25. A non-transitory program storage device readable by a computer, tangibly embodying a program of instructions executed by the computer to perform operations for predicting a cancer staging score from medical image data, the operations comprising:
receiving patient data for a plurality of patients, wherein patient data for each of said plurality of patients includes one or more of an image volume of a suspected tumor in an organ, blood test data, demographic data, and ground truth tumor staging scores for the suspected tumor in said organ;
extracting features from said patient data, wherein features from said demographic data include a patient's weight, height, age, body mass index, body surface area, organ size, any past history of cancer occurrence, and any health index test results; and
using the features extracted from said patient data to train a classifier to predict a cancer staging score for a new patient from one or more of an image volume of a suspected tumor in said organ, patient blood test data and patient demographic data of that new patient.

26. The computer readable program storage device of claim 25, wherein the image volume comprises one or more of an anatomical image volume, a functional image volume, or a fused anatomical/functional image volume, and features extracted from said image volume include one or more of anatomical features and functional features from said organ.

27. The computer readable program storage device of claim 26, wherein extracting anatomical and functional features of said organ from said image volume comprises:
segmenting the organ in each of the anatomical and functional images to define one or more regions of interest (ROIs); and
extracting anatomical and functional features from the one or more regions of interest.

28. The computer readable program storage device of claim 27, wherein a region of interest (ROI) is one of the whole organ or a segment of the organ.

29. The computer readable program storage device of claim 26, wherein anatomical features include a volume of an ROI, a surface area of the ROI, a diameter of the ROI, texture features associated with the ROI, and geometric descriptors of a surface of the ROI.

30. The computer readable program storage device of claim 29, wherein texture features are calculated from a Gray Level Co-occurrence Matrix of the ROI.

31. The computer readable program storage device of claim 26, wherein functional features include a standard uptake value, an apparent diffusion coefficient, a permeability surface area product per unit volume of tissue, a fraction of plasma per unit volume of tissue, and a rate constant of an efflux of contrast media from extracellular space back to plasma.

32. The computer readable program storage device of claim 26, wherein imaging modalities that capture anatomical information include magnetic resonance imaging (MRI), computed tomography (CT), ultrasound (US), optical coherence tomography (OCT), imaging modalities that capture functional information include positron emission tomography (PET), single photon emission computed tomography (SPECT), dynamic contrast enhanced MRI (DCE-MRI), and diffusion weighted MRI (DW-MRI), and a fused anatomical/functional modality that captures anatomical and functional information includes any combination of a modality that captures anatomical information and a modality that captures functional information.

33. The computer readable program storage device of claim 25, wherein the classifier is trained using an image-based boosting ridge regression method.

34. The computer readable program storage device of claim 27, wherein said classifier predicts a local staging score for each segment or ROI of the organ and a global staging score by combining local staging scores for each segment or ROI.

35. The computer readable program storage device of claim 25, wherein the organ is a prostate gland, image features arc extracted from a fused MR/PET image, features from said blood test data include a prostate specific antigen (PSA) level, a PSA velocity, a PSA density, and a prostate health index, and the predicted cancer staging score is a Gleason score.

36. The computer readable program storage device of claim 25, wherein the organ is a lung, image features are extracted from a fused MR/PET image, and the predicted cancer staging score is a TNM score.

37. The computer readable program storage device of claim 25, wherein the organ is a breast, image features arc extracted from a fused MR/PET image, and the predicted cancer staging score is one of a Nottingham Score or a Scarf-Bloom-Richardson Score.

* * * * *